(12) United States Patent
Kurimura et al.

(10) Patent No.: US 7,878,205 B2
(45) Date of Patent: Feb. 1, 2011

(54) MANUFACTURING METHOD FOR QPM WAVELENGTH CONVERTER ELEMENTS, QPM WAVELENGTH CONVERTER ELEMENT, AND MEDICAL LASER APPARATUS USING IT

(75) Inventors: Sunao Kurimura, Kurimura (JP); Tsuyoshi Yamada, Toyota (JP)

(73) Assignees: National Institute for Materials Science, Tsukuba-shi (JP); Nidek Co., Ltd., Gamagori-shi (JP)

(*) Notice: Subject to any disclaimer, the term of this patent is extended or adjusted under 35 U.S.C. 154(b) by 36 days.

(21) Appl. No.: 11/905,933

(22) Filed: Oct. 5, 2007

(65) Prior Publication Data

US 2008/0046043 A1    Feb. 21, 2008

Related U.S. Application Data

(62) Division of application No. 10/795,255, filed on Mar. 9, 2004, now Pat. No. 7,329,316.

(30) Foreign Application Priority Data

Mar. 14, 2003  (JP) .............................. 2003-069035
Mar. 14, 2003  (JP) .............................. 2003-069036

(51) Int. Cl.
*A61B 19/00*    (2006.01)
*G02F 1/35*    (2006.01)

(52) U.S. Cl. .............................. 128/898; 117/3; 607/89; 359/326; 372/44.011

(58) Field of Classification Search .................. 606/10; 607/88, 89; 117/2–10; 359/326–332; 372/43.01, 372/44.011
See application file for complete search history.

(56) References Cited

U.S. PATENT DOCUMENTS

| 3,932,777 | A | * | 1/1976 | King ........................... 310/311 |
| 5,264,959 | A | * | 11/1993 | Barker et al. ................. 359/328 |
| 6,428,532 | B1 | * | 8/2002 | Doukas et al. ................. 606/9 |
| 7,206,122 | B2 | * | 4/2007 | Kurimura et al. ............ 359/326 |

FOREIGN PATENT DOCUMENTS

| GB | 580965 | | 9/1946 |
| GB | 601243 | | 4/1948 |
| JP | 2002-276002 | * | 9/2002 |

(Continued)

OTHER PUBLICATIONS

Oyo Buturi, "Twin-controlled crystal quartz for quasi-phase-matched wavelength conversion in ultraviolet region"; vol. 69, No. 5; pp. 0548-0552; 2000.

(Continued)

*Primary Examiner*—Ahmed M Farah
(74) *Attorney, Agent, or Firm*—Oliff & Berridge, PLC

(57) ABSTRACT

A manufacturing method for quasi phase matching (QPM) wavelength converter elements using crystal quartz as a base material in which twins are periodically induced, comprises a step of periodically inducing the twins by applying a stress onto a crystal quartz substrate as the base material so that an angle θ of a direction in which the stress is applied relative to a Z axis of the crystal quartz is 60°<θ<90°.

3 Claims, 4 Drawing Sheets

FOREIGN PATENT DOCUMENTS

JP  A-2003-075876  3/2003

OTHER PUBLICATIONS

S.M. Shiau et al.; "Temperature Dependence of Ferrobielastic Switching in Quartz"; Mat. Res. Bull., vol. 19, pp. 831-836; 1984.

Annual Report 1997-98, "Twinned quartz for quasi-phasematched ultraviolet generation"; Center for Nonlinear Optical Materials, Stanford University.

Tsuyoshi Yamada et al.; "Periodical Twin Structure in Quartz with High Aspect Ratio"; The 1$^{st}$ NIMS International Conference; Mar. 17-19, 2003; National Institute for Materials Science.

Extended Abstracts (The 50 the Spring Meeting, 2003); Mar. 27-Mar. 30, 2003; The Japan Society of Applied Physics and Related Societies.

Extended Abstracts (The 64$^{th}$ Autumn Meeting, 2003); Aug. 30-Sep. 2, 2003; The Japan Society of Applied Physics.

"Twin control in crystal quartz for second harmonic generation of a blue-violet laser"; Extended Abstracts (The 63$^{rd}$ Meeting; Sep. 2003; The Japan Society of Applied Physics and Related Societies.

Sunao Kurimura et al.; "Periodical twinning for quasi-phasematached quartz" Conference on Lasers and Electro-Optics; 2003; Quantum Electronics & Laser Science Conference; Jun. 1-6, 2003.

Martin, Fejer; "Twin-controlled cryctal quartz for quasi-phase-matched wavelength conversion in ultraviolent region"; 2000; pp. 548-552.

Kurimura et al., "Shigai hacho henkan mezashita giji iso seigo suisho/ Twin-Controlled Crystal Quartz for Quasi-Phase-Matched Wavelength Conversion in Ultraviolet Region," *Oyo Butsuri*, vol. 69, No. 5, 2000, pp. 548-552.

Boy J et al., "Quartz Crystal Twinning Under Mechanical Stress: Experimental Measurements," *New York, IEEE*, 1996, pp. 155-160.

Newnham et al., "Symmetry of Secondary Fcrroics. II," *Materials Research Bulletin*, Aug. 1974, vol. 9, No. 8, pp. 1021-1031.

Newnham et al., "Polycrystalline Secondary Ferroics," *Materials Research Bulletin*, Oct. 1976, vol. 11, No. 10, pp. 1273-1284.

Shiau et al., "Temperature Dependence of Ferrobielastic Switching in Quartz," *Master Research Bulleting*, Jul. 1984, vol. 19, No. 7, pp. 831-836.

Uno, "Acoustic Wave Devices Using Artificial Twin Quartz Plates," *Japanese Journal of Applied Physics*, May 1996, vol. 35, No. 5B, pp. 2975-2979.

*The Institute of Electrical and Electronics Engineers*: "IEEE Standard on Piezoelectricity—ANSI/IEEE Std. 176-1987," 1988, pp. 25-28.

* cited by examiner

MANUFACTURING METHOD FOR QPM WAVELENGTH CONVERTER ELEMENTS, QPM WAVELENGTH CONVERTER ELEMENT, AND MEDICAL LASER APPARATUS USING IT

This is a Division of application Ser. No. 10/795,255 filed Mar. 9, 2004. The disclosure of the prior application is hereby incorporated by reference herein in its entirety.

FIELD OF THE INVENTION

The present invention relates to a manufacturing method for quasi phase matching (QPM) wavelength converter elements (devices) using crystal quartz as the base material (host material), a QPM wavelength converter element (device), and a medical laser apparatus using it.

DESCRIPTION OF RELATED ART

In recent years, many research and development attempts on solid lasers using wavelength converter elements have been made. More recently, in particular, the establishment of a high voltage application method has much facilitated fabrication of QPM wavelength converter elements using ferroelectric crystals. This has enabled high efficiency wavelength conversion to be accomplished in the visible to infrared wavelength ranges.

For wavelength conversion in the ultraviolet wavelength range, fabrication of QPM wavelength converter elements from $BaMgF_4$ crystals, which are ferroelectric, is attempted. However, the $BaMgF_4$ crystals have a very low effective nonlinear constant. For this reason, fabrication of QPM wavelength converter elements from crystal quartz ($SiO_2$), whose effective nonlinear constant is about 10 times as great as that of the $BaMgF_4$ crystals, is under study.

It has to be noted here that in the crystal quartz, as it is a non-ferroelectric, the application of high voltage does not work for fabricating a QPM structure. Therefore, an alternative method of inducing periodic twins (hemitropes) by applying a stress to the crystal quartz and thereby realizing a polarity-inverted structure has been proposed. This results in a change in the sign of nonlinear optical constant d11 among the twins, which enables QPM in the period of twin alignment (arrangement).

Incidentally, the application of the stress to the crystal quartz was previously considered to cause the twins to grow along the Z axis of the crystal quartz. For this reason, the stress application was so carried out that the angle θ of the stress application relative to the Z axis of the crystal quartz is 0°<θ<60°. Further, in inducing the twins in the crystal quartz, the stress application was performed while uniformizing the temperature distribution of the crystal quartz in the vicinity of the phase transition temperature (573° C.) of the crystal quartz.

In this way, fabrication of QPM wavelength converter elements which would function as wavelength converter elements when the direction of the Z axis of the crystal quartz is made substantially orthogonal to the incident light vector is attempted by forming the polarity-inverted structure by inducing the periodic twins.

However, the conventional manufacturing method involves a problem that the aspect ratio in the growth of the twins is extremely low in addition to low controllability of the twins. As a result, it has been impossible to obtain practical usable QPM wavelength converter elements in bulk using the crystal quartz as the base material.

SUMMARY OF THE INVENTION

The present invention has been made in view of the above circumstances and has an object to overcome the above problems and to improve the control of the twins in the crystal quartz, realize the growth of the twins in a high aspect ratio, and provide a manufacturing method for QPM wavelength converter elements permitting in particular for practical use wavelength conversion to the ultraviolet range, such a QPM wavelength converter element, and a medical laser apparatus using it.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a manufacturing method for quasi phase matching (QPM) wavelength converter elements using crystal quartz as a base material in which twins are periodically induced, comprising: a step of periodically inducing the twins by applying a stress onto a crystal quartz substrate as the base material so that an angle θ of a direction in which the stress is applied relative to a Z axis of the crystal quartz is 60°<θ<90°.

According to another aspect, the present invention provides a manufacturing method for quasi phase matching (QPM) wavelength converter elements using crystal quartz as a base material in which twins are periodically induced, comprising: a stress application step of periodically inducing the twins by applying a stress onto a crystal quartz substrate as the base material; and a heat treatment step of keeping a temperature between two planes of the crystal quartz substrate orthogonal to a direction in which the stress is applied at or below a phase transition temperature of the crystal quartz and creating a temperature difference between the two planes.

According to another aspect, the present invention provides a quasi phase matching (QPM) wavelength converter element whose base material is crystal quartz in which twins are periodically induced by applying a stress, wherein interfaces of the twins are formed in a plane containing a Y axis of the crystal quartz and the twins are formed in a direction of a Z axis of the crystal quartz periodically.

According to another aspect, the present invention provides a medical laser apparatus comprising: a laser light source; and a wavelength converter element for converting the wavelength of a laser beam from the laser light source, wherein the wavelength converter element is the QPM wavelength converter element mentioned above.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
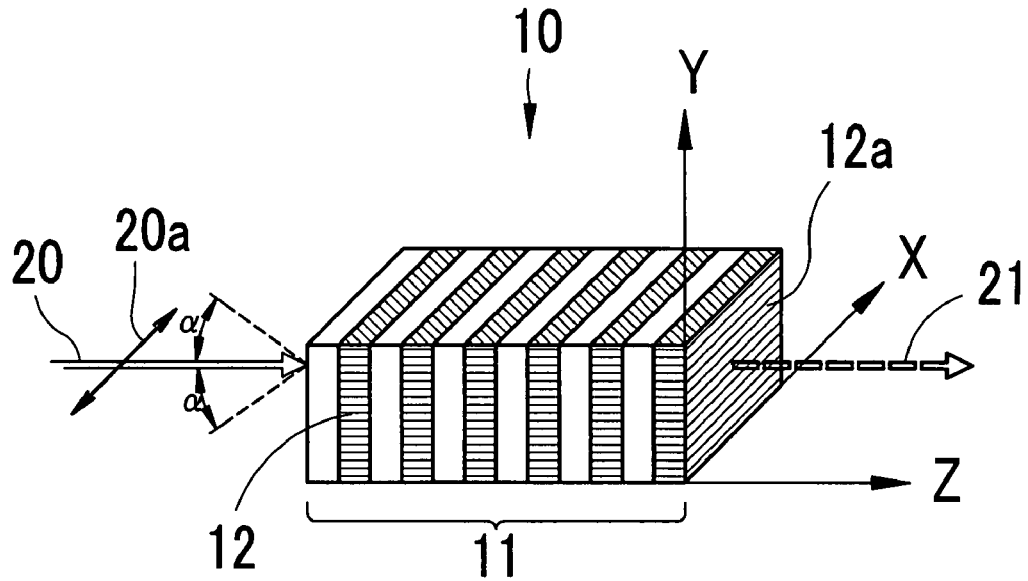
FIG. 1 illustrates a schematic structure of a quasi phase matching wavelength converter element (QPM crystal quartz) in an embodiment of the invention and wavelength conversion using the QPM crystal quartz.

A preferred embodiment of the present invention will be described below with reference to the accompanying drawings. FIG. 1 illustrates a schematic structure of a quasi phase matching wavelength converter element (QPM crystal quartz), which is the preferred embodiment of the invention and wavelength conversion using the QPM crystal quartz.

A quasi phase matching wavelength converter element (hereinafter referred to as QPM crystal quartz) 10 uses crystal quartz 11 as the base material. Crystal quartz has many useful features including excellent chemical stability, a high damage threshold, transparency up to the ultraviolet region of 150 nm and a lower cost than other crystals. Thus, the crystal quartz has advantages as a material for wavelength converter elements for the generation of ultraviolet rays.

Twins in the crystal quartz were previously considered to grow in the direction of the Z axis of the crystal quartz when the twins in the crystal quartz were caused to grow by applying a stress. However, experimental findings by the present inventors have revealed that twins at first grow in the direction of the Y axis of the crystal quartz, followed by growth in the direction of the Z axis.

This indicates that the QPM crystal quartz 10 has the following structure. In the QPM crystal quartz 10, periodic twins 12 are induced in the direction of the Z axis of the crystal quartz 11 as the base material, resulting in the formation of a structure whose polarity is periodically inverted. The interfaces 12$a$ of the twins 12 are formed in a plane containing the Y axis of the crystal quartz 11. By bringing a fundamental wave beam 20 into incidence in the direction of the Z axis of this QPM crystal quartz 10, a wavelength-converted beam 21, which is the second harmonic of the fundamental wave beam 20, is caused to be emitted.

The incidence vector of the fundamental wave beam 20 should preferably be, but not absolutely required to be, parallel to the direction of the Z axis of the crystal quartz 11 (substantially orthogonal to the plane of the ZY axes in FIG. 1). Since QPM is achieved in the crystal quartz 11 because the sign of its nonlinear optical constant d11 is periodically inverted, the wavelength-converted beam 21 can be taken out if the polarized beam 20$a$ of the fundamental wave beam 20 at least has an X axis component. For practical purposes, where the angle formed by the direction of the Z axis and the incidence vector of the fundamental wave beam 20 is represented by α, α should preferably be 0°≦α≦30°.

Figure 2:
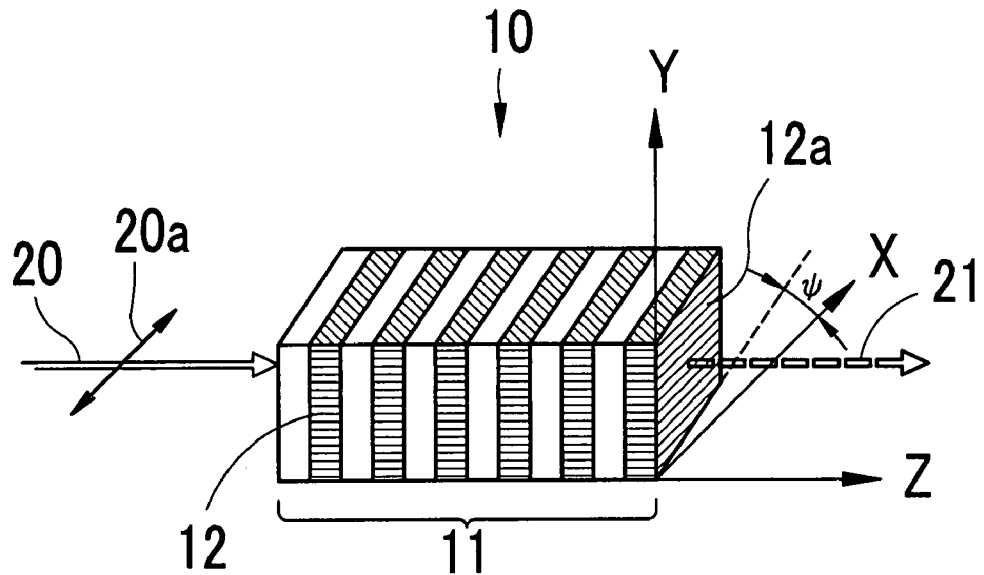
FIG. 2 illustrates a schematic structure of QPM crystal quartz in another embodiment and wavelength conversion using the QPM crystal quarts.

Although the interfaces 12$a$ are supposed to contain the X axis of the crystal quartz 11 too in their planes as illustrated in FIG. 1, the interfaces 12$a$ may as well be so formed as not to contain the X axis of the crystal quartz 11 in their planes as illustrated in FIG. 2. In taking out the wavelength-converted beam 21, however, the polarized beam 20$a$ of the fundamental wave beam 20 needs to have the X axis component. Thus for this reason, so that the periodic twins 12 be formed in the direction of the Z axis, the angle ψ formed by the interfaces 12$a$ and the X axis is at least prevented from being perpendicular.

Figure 3A:
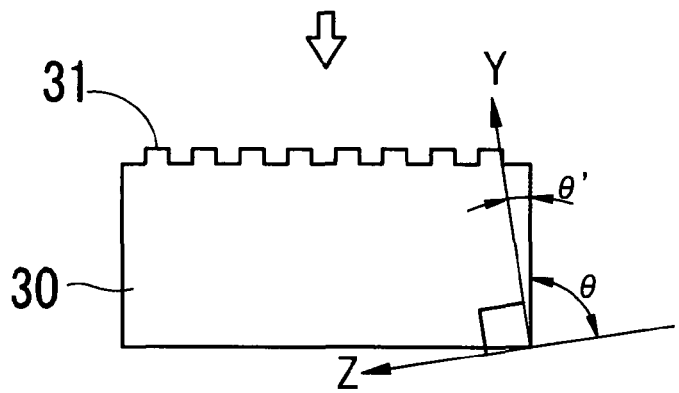
FIGS. 3A to 3C are views to explain a manufacturing method for the QPM crystal quartz in the embodiment.

Next will be described the manufacturing method of the QPM crystal quartz 10 with reference to FIG. 3. First as shown in FIG. 3A, the angle θ of the direction in which the stress is applied relative to the Z axis of the crystal quartz is set to 60°<θ<90°, the cut-out orientation θ′ relative to the Y axis of the crystal quartz is set to 0°<θ′<30°. The reason why the angle θ of the direction in which the stress is applied relative to the Z axis of the crystal quartz is set to 60°<θ<90° is that twins have been found to grow in the direction of the Y axis of the crystal quartz. Preferably the angle θ of the direction in which the stress is applied relative to the Z axis of the crystal quartz should be 80°≦θ≦88° (2°≦θ′≦20°). Incidentally in this embodiment, a crystal quartz substrate 30 of 3 mm in thickness cut in an orientation of 5° from the Y axis (=85° from the Z axis) is used.

Figure 4:
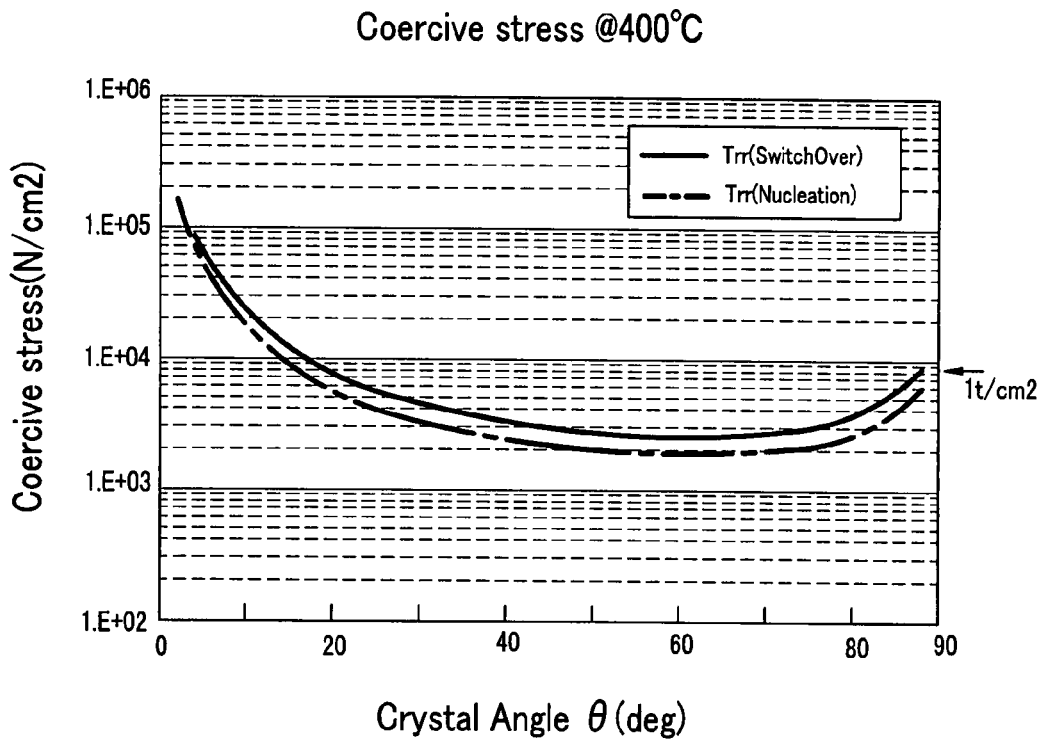
FIG. 4 shows a result of computation of angle-dependence of coercive stress.

Now, FIG. 4 shows the result of computation of the angle-dependence of coercive stress at a temperature of 400° C. In the diagram, the curve in one-dot chain line represents the stress level at which the growth of twins begins and that in solid line is where the growth of twins is completed. Previously, the angle θ of the direction of stress application relative to the direction of the Z axis was set to 0°<θ≦60°, e.g. θ=13°. This was because twins were considered to grow in the direction of the Z axis. By contrast to it, in this embodiment of the invention the angle θ of the direction of stress application relative to the direction of the Z axis is set to 60°<θ<90°. This is because twins have been found to grow in the direction of the Y axis of the crystal quartz.

Next, machining is done to form on the surface of the crystal quartz substrate 30 a stepped structure 31 having level gaps in a period of realizing the desired wavelength conversion. The stepped structure 31 can be formed by photolithography. The depth of the step is, e.g., 2 μm. This stepped structure 31 may be on the first heater block 40 side on which the stress would be applied to the crystal quartz substrate 30.

Figure 3B:
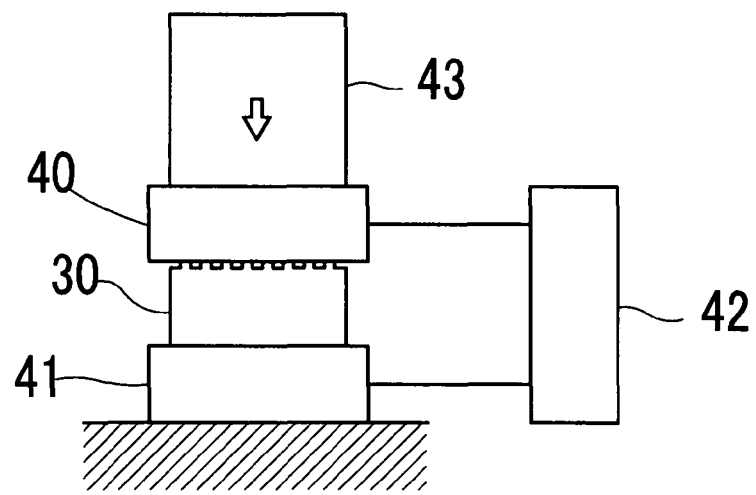

Next, the crystal quartz substrate 30, over which the stepped structure 31 is formed, is sandwiched between the first heater block 40 and a second heater block 41 as shown in FIG. 3B, and a uniform uniaxial vertical stress is applied with a stress applying device 43. In this process, the temperature T1 of the first heater block 40 arranged on the stepped structure 31 side and the temperature T2 of the other second heater block 41 are kept at or below the phase transition temperature (573° C.). Also, in order to keep the temperature T1 higher than the temperature T2 (T1>T2), a temperature difference ΔT is created between two planes orthogonal to the direction of stress application. For instance, the temperature difference ΔT of 175° C. is created by setting T1 to 375° C. and T2 to 200° C. The heater blocks 40 and 41 are controlled by a control device 42 to be individually variable in temperature.

Figure 3C:
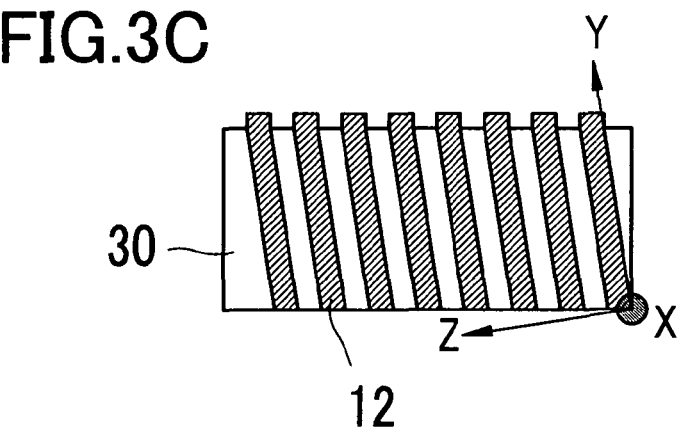

Then, in a state in which the temperature difference ΔT is created at a level below the phase transition temperature between the two planes orthogonal to the direction of stress application, the uniform vertical stress is applied with the stress applying device 43. This causes anisotropic twins (twins growing in the direction of a specific axis of the crystal quartz) reflecting the level gap of the stepped structure 31 over the crystal quartz substrate 30 in the direction of the Y axis as shown in FIG. 3C, and the crystal quartz substrate 30 having periodic twins in the direction of the Z axis is obtained. By cutting and grinding this crystal quartz substrate 30 so that the end face of the crystal quartz and the Z axis are substantially orthogonal to each other, the QPM crystal quartz 10 illustrated in FIG. 1 is obtained.

In an experiment by the present inventors, when a stress was applied while the temperature was simply raised to the vicinity of the phase transition temperature without differentiating the temperature between the two planes orthogonal to the direction of stress application, isotropic twins (twins growing at random without distinction between the Y axis and the Z axis of the crystal quartz) emerged, and sometimes no twins reflecting the level gap were induced from the stepped structure 31 side. By contrast, when the temperature difference ΔT was created between the two planes orthogonal to the direction of stress application, twins reflecting the level gap were induced from the stepped structure 31 side where temperature was higher, and they grew long toward the lower temperature side.

Further in the experiment by the present inventors, when the temperature T2 on the second heater block 41 side was gradually raised with the temperature T1 on the first heater block 40 side kept at 375° C., anisotropic twins grew until T2 reached 200° C. Then, the anisotropic twins grew longer with a rise in the temperature T2. At T2=225° C., however, isotropic twins began to grow from the lower temperature side (the second heater block 41 side). Therefore, no twins are induced from the other side of the stepped structure 31, and in order to selectively cause anisotropic twins to grow from the stepped structure 31 side, the temperature T2 on the lower temperature side (the second heater block 41 side) should be T2<225° C. Preferably, it should be T2≦220° C.

On the other hand, when the temperature on the higher temperature side (the first heater block 40 side) was gradually raised from 375° C. with T2 being kept at 200° C., only anisotropic twins grew until T1 reached 450° C. However, at T1=475° C., isotropic twins instead of anisotropic twins came to grow predominantly. Therefore, in order to selectively cause anisotropic twins to grow from the stepped structure 31 side, the temperature T1 on the higher temperature side (the first heater block 40 side) should be higher than T2 and 250° C.<T1<475° C. Preferably, T1 should be 300° C.≦T1≦470° C. More preferably, T1 should be 375° C.≦T1≦450° C.

Figure 5:
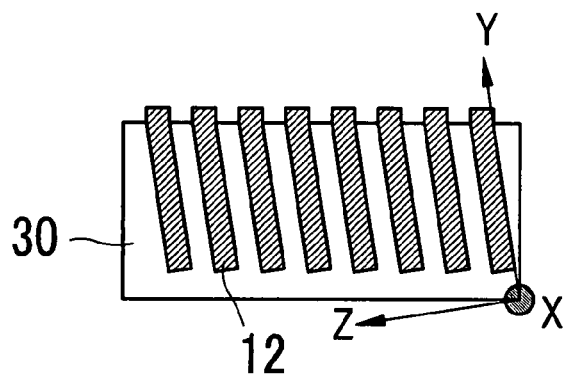
FIG. 5 is a view to explain a manufacturing method for the QPM crystal quartz in another embodiment.

Although the diagram of FIG. 3C illustrates a case in which the twins 12 growing in the direction of the Y axis penetrate the crystal quartz substrate 30 as far as its under side (the other side of the stepped structure 31), they may as well be caused to grow to some middle point as shown in FIG. 5 instead of letting the twins 12 penetrate the crystal quartz substrate 30 as far as its under side (the other side of the stepped structure 31). Since the twins grow in the direction of the Z axis after they have grown in the direction of the Y axis, they will be easier to control if they are now allowed to penetrate the crystal quartz substrate 30 as far as its under side. The length of the twins can be controlled according to the conditions of the temperatures T1 and T2. If the twins are to be relatively short, T2 should be lower than 200° C. and ΔT, larger than 175° C. Advisably, in using the QPM crystal quartz 10 obtained by not letting the twins penetrate the crystal quartz substrate 30 as far as its under side, the fundamental wave beam should be let pass the region in which the twins are formed.

Figure 6:
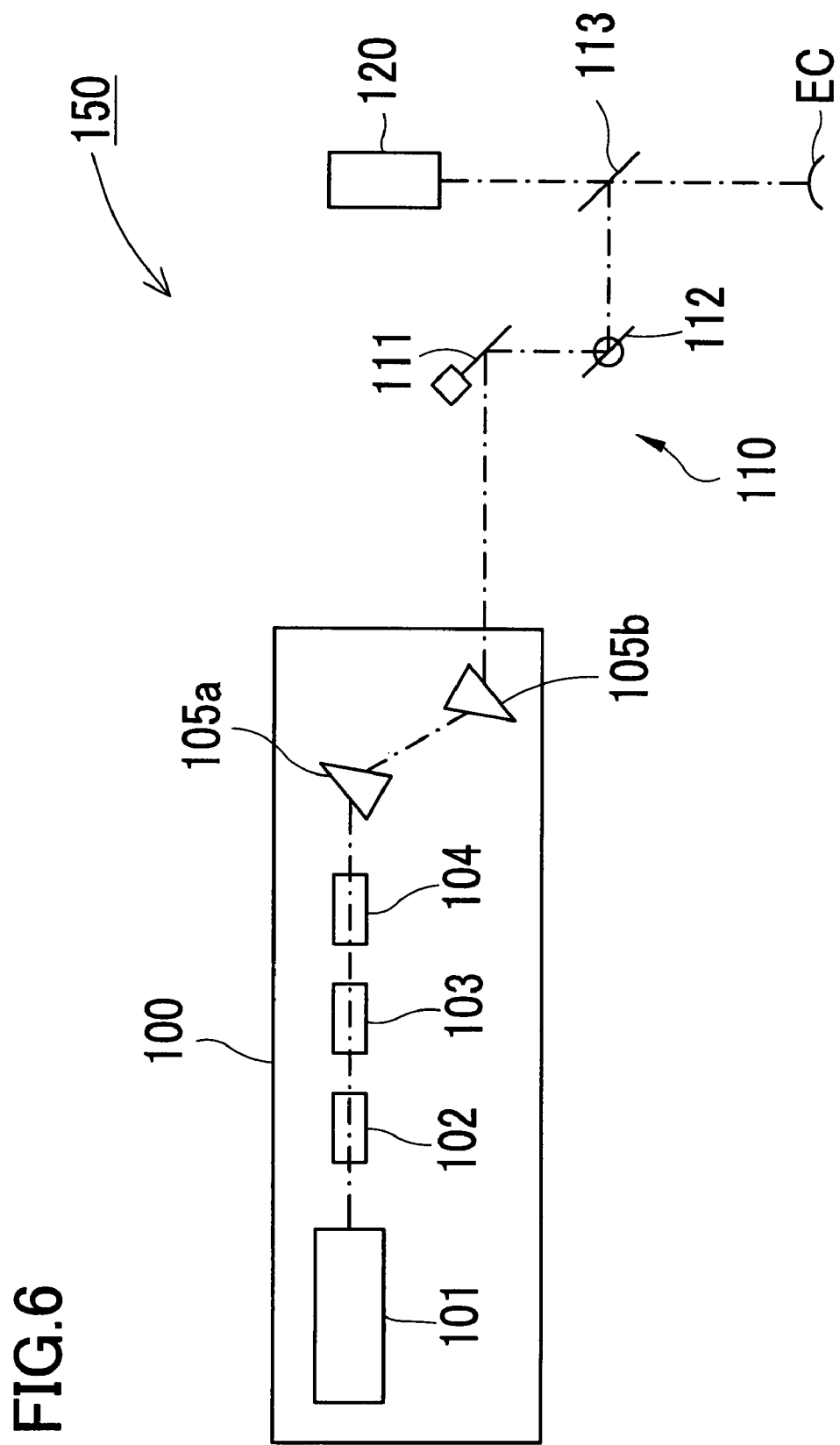
FIG. 6 illustrates a schematic structure of a medical laser apparatus using the QPM crystal quartz in the embodiment.

A description of a laser apparatus 150 using the QPM crystal quartz 10 obtained as described above will follow, with reference to FIG. 6. FIG. 6 illustrates a schematic structure of the laser apparatus 150. Here it will be described, by way of example, with reference to a medical laser apparatus for cornea ablation using a wavelength-converted beam in the ultraviolet region.

An Nd:YAG solid laser light source 101, wavelength converter elements 102, 103 and 104, and a pair of prisms 105a and 105b are arranged in a laser light source unit 100 provided in the laser apparatus 150. The solid laser light source 101 emits a pulse laser beam of 1064 nm. The wavelength converter element 102 generates a converted beam of 532 nm in wavelength by converting a fundamental wave beam of 1064 nm in wavelength into its second harmonic. The wavelength converter element 103 generates a converted beam of 266 nm in wavelength by converting the converted beam of 532 nm to its second harmonic. The wavelength converter element 104 generates a converted beam of 213 nm in wavelength, which is the sum-frequency beam of the wavelength 1064 nm of the components not converted by the wavelength converter element 102 and the wavelength 266 nm converted by the wavelength converter element 103. Here, the QPM crystal quartz 10 shown in FIG. 1 are used as the wavelength converter elements 103 and 104 for wavelength conversion into the ultraviolet region. As the wavelength converter element 102, a KTP crystal or the like can be used, but the same QPM crystal quartz 10 can be used as well.

The prism 105a separates the laser beams of different wavelengths from one another. Out of the laser beams separated by the prism 105a, that of 213 nm in wavelength comes incident on the prism 105b, and other beams are shielded by a shield element (not shown). The laser beam of 213 nm in wavelength, as the beam for therapeutic use, is adjusted in the output direction, and emitted from the laser light source unit 100.

A guiding optical system 110 is provided with a scanning optical system consisting of two galvano-mirrors 111 and 112 and a dichroic mirror 113. The dichroic mirror 113 has a characteristic of reflecting a laser beam of 213 nm and transmitting visible beams. A laser beam scanned at high speed by the two galvano-mirrors 111 and 112 is then reflected by the dichroic mirror 113 to be guided to a cornea Ec of the patient's eye. Although the optical system on the optical path from the laser light source unit 100 to the galvano-mirror 111 is not illustrated, a mirror for reflecting the laser beam, an optical system for shaping the laser beam into a circular spot, and a corrective optical system for correcting its energy distribution are appropriately arranged. Advisably, the spot size of the laser beam in this laser apparatus 150 should be about 1 mm on the cornea Ec. Over the dichroic mirror 113 is arranged an observation optical system 120.

A corneal surgery using this laser apparatus 150 will be briefly described below. When data on the corneal surgery is entered into the laser apparatus 150, a control unit (not shown) obtains control data for laser irradiation on the basis of the corneal surgery data. For instance, where myopia is to be corrected, a combination of superposition of a pulse laser and the number of pulses (duration of irradiation) is used as the control data for laser irradiation for ablation which is to be deep in the central part of the cornea Ec and progressively shallower toward the periphery. An ultraviolet beam of 213 nm is supplied from the laser light source unit 100 by the wavelength conversion described above, and scanning operations by the galvano-mirrors 111 and 112 controlled on the basis of the control data guide the laser beam onto the cornea Ec. This causes the cornea Ec to be ablated into the desired shape.

As described above, wavelength conversion by the QPM crystal quartz 10 is applicable in particular to laser apparatuses which conduct wavelength conversion to laser beams in the ultraviolet region, and suitable for use in laser apparatuses for medical use.

As described above, according to the present invention, control of twins in crystal quartz can be improved and the growth of twins realized in a high aspect ratio. Furthermore, it enables wavelength conversion of ultraviolet rays for practical purposes and its suitable application to laser apparatuses for medical use.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A quasi phase matching (QPM) wavelength converter comprising crystal quartz with periodically-arrayed twins manufactured by a method comprising:
applying stress to crystal quartz so that an angle θ of a direction in which the stress is applied relative to a Z axis of the crystal quartz is 60°<θ<90°, wherein:
interfaces of the twins lie in a plane including a Y axis of the crystal quartz; and
the twins are periodically arrayed in a direction of the Z axis of the crystal quartz.

2. The QPM wavelength converter element according to claim 1, wherein
the interfaces of the twins lie in a plane including an X axis of the crystal quartz.

3. A medical laser apparatus comprising:
a laser light source; and
a wavelength converter element for converting the wavelength of a laser beam from the laser light source, wherein
the wavelength converter element is the QPM wavelength converter element according to claim 1.

* * * * *